(12) United States Patent
Perie

(10) Patent No.: US 10,723,657 B2
(45) Date of Patent: Jul. 28, 2020

(54) SINTERED ALUMINA-BASED AND ZIRCONIA-BASED PRODUCT

(71) Applicant: SAINT-GOBAIN CENTRE DE RECHERCHES ET D'ETUDES EUROPEEN, Courbevoie (FR)

(72) Inventor: Thomas Perie, Avignon (FR)

(73) Assignee: SAINT-GOBAIN CENTRE DE RECHERCHES ET D'ETUDES EUROPEEN, Courbevoie (FR)

( * ) Notice: Subject to any disclaimer, the term of this patent is extended or adjusted under 35 U.S.C. 154(b) by 0 days.

(21) Appl. No.: 15/749,034

(22) PCT Filed: Jul. 13, 2016

(86) PCT No.: PCT/EP2016/066697
§ 371 (c)(1),
(2) Date: Jan. 30, 2018

(87) PCT Pub. No.: WO2017/016879
PCT Pub. Date: Feb. 2, 2017

(65) Prior Publication Data
US 2018/0230058 A1   Aug. 16, 2018

(30) Foreign Application Priority Data
Jul. 30, 2015   (FR) .................................... 15 57315

(51) Int. Cl.
*C04B 35/488* (2006.01)
*G04B 37/22* (2006.01)
(Continued)

(52) U.S. Cl.
CPC ........ *C04B 35/4885* (2013.01); *A44C 27/003* (2013.01); *A61C 13/083* (2013.01);
(Continued)

(58) Field of Classification Search
CPC .......................... C04B 35/4885; C04B 35/119
See application file for complete search history.

(56) References Cited

U.S. PATENT DOCUMENTS 8,614,001 B2 * 12/2013 Nonnet ................. C04B 35/119
428/402
2009/0317767 A1 * 12/2009 Burger ................ C04B 35/4885
433/201.1
2012/0082849 A1 * 4/2012 Nonnet ................. C04B 35/119
428/402

FOREIGN PATENT DOCUMENTS

JP            2006104024 A * 4/2006

OTHER PUBLICATIONS

Machine translation of JP 200604024, Apr. 2006. (Year: 2006).*
(Continued)

*Primary Examiner* — Karl E Group
(74) *Attorney, Agent, or Firm* — Oliff PLC

(57) ABSTRACT

Sintered product having a chemical analysis such that, in percentage by mass based on the oxides: $ZrO_2$ partially stabilized with $CeO_2$ and $Y_2O_3$ is balance to 100%; $Al_2O_3$ is >10% and <19%; additive chosen from CaO, manganese oxides, ZnO, praseodymium oxides, SrO, copper oxides, $Nd_2O_3$, BaO, iron oxides, and mixtures thereof is 0.2-6%; impurities are <2%; and $CeO_2$ and $Y_2O_3$ being present in amounts such that, as a molar percentage on the basis of the sum of $ZrO_2$, $CeO_2$ and $Y_2O_3$, $CeO_2$ is ≥2.5 mol % and <5.5 mol %, and $Y_2O_3$ is 0.5-2 mol %.

17 Claims, 1 Drawing Sheet

(51) Int. Cl.
  *A61C 13/083* (2006.01)
  *A44C 27/00* (2006.01)
  *A61K 6/818* (2020.01)
  *A61K 6/822* (2020.01)

(52) U.S. Cl.
  CPC .............. *A61K 6/818* (2020.01); *A61K 6/822* (2020.01); *G04B 37/225* (2013.01); *C04B 2235/3208* (2013.01); *C04B 2235/3213* (2013.01); *C04B 2235/3215* (2013.01); *C04B 2235/3224* (2013.01); *C04B 2235/3225* (2013.01); *C04B 2235/3227* (2013.01); *C04B 2235/3229* (2013.01); *C04B 2235/3246* (2013.01); *C04B 2235/3262* (2013.01); *C04B 2235/3272* (2013.01); *C04B 2235/3281* (2013.01); *C04B 2235/3284* (2013.01); *C04B 2235/5445* (2013.01); *C04B 2235/6562* (2013.01); *C04B 2235/72* (2013.01); *C04B 2235/77* (2013.01); *C04B 2235/783* (2013.01); *C04B 2235/785* (2013.01); *C04B 2235/786* (2013.01); *C04B 2235/788* (2013.01); *C04B 2235/96* (2013.01); *F05D 2230/22* (2013.01)

(56) References Cited

OTHER PUBLICATIONS

Urabe et al. "Phase transformation and lattice constants of zirconia solid solutions in the system Y2O3—CeO2—ZrO2". Materials Science Forum vols. 34-36, pp. 147-152, 1988.
Mendelson et al. "Average Grain Size in Polycrystalline Ceramics". Am. Cerm. Soc., vol. 52, No. 8, pp. 443-446, 1969.
Brunauer et al. "Adsorption of Gases in Multimolecular Layers." Journal of American Chemical Society vol. 60, pp. 309-319, 1938.

* cited by examiner

SINTERED ALUMINA-BASED AND ZIRCONIA-BASED PRODUCT

TECHNICAL FIELD

The invention relates to a sintered product based on alumina and on zirconia, to a particulate mixture that makes it possible to obtain such a product, and also to a process for manufacturing said product.

BACKGROUND OF THE INVENTION

Among refractory products, a distinction is made between fused cast products and sintered products.

Unlike sintered products, fused cast products usually comprise a very abundant intergranular glassy phase which fills a network of crystalline grains. The problems encountered in their respective applications by sintered products and by fused cast products, and the technical solutions adopted for solving them, are therefore generally different. Furthermore, due to the significant differences between the manufacturing processes, a composition developed for manufacturing a fused cast product is not a priori able to be used as such for manufacturing a sintered product, and vice versa.

Sintered products are obtained by mixing appropriate raw materials then forming this mixture in the green state and firing the resulting green part at a temperature and for a time that are sufficient for sintering this green part.

Sintered products, depending on their chemical composition, have different properties and are therefore intended for very different industries.

Among ceramic sintered products, quadratic yttria-stabilized zirconia products, typically comprising a molar amount of $Y_2O_3$ equal to 3%, have a high rupture stress and a high hardness.

Ceria-stabilized zirconia products, typically comprising a molar amount of $CeO_2$ equal to 12%, have a very high toughness, greater than that of yttria-stabilized zirconia products, but a lower rupture stress and a lower hardness.

There is therefore a need for a sintered ceramic product that has a better compromise of hardness, toughness and modulus of rupture.

One aim of the invention is to at least partially meet this need.

SUMMARY OF THE INVENTION

The invention proposes a sintered product having a chemical analysis such that, as percentages by weight on the basis of the oxides,
  $ZrO_2$ partially stabilized with $CeO_2$ and $Y_2O_3$: balance to 100%,
  $Al_2O_3$: >10% and <19%
  additive chosen from CaO, manganese oxides, ZnO, praseodymium oxides, SrO, copper oxides, $Nd_2O_3$, BaO, iron oxides, and mixtures thereof: 0.2-6%,
  impurities: <2%,
  $CeO_2$ and $Y_2O_3$ being present in amounts such that, as a molar percentage on the basis of the sum of $ZrO_2$, $CeO_2$ and $Y_2O_3$,
  $CeO_2$: ≥2.5 mol % and <5.5 mol % and
  $Y_2O_3$: 0.5-2 mol %.

Preferably, the particle size distribution of the sintered product is such that:
  the mean size of the grains having a shape factor of less than 2.5, or "compact grains", is less than 2 μm, the mean length of the aluminous elongated nodules is less than 20 μm, an aluminous elongated nodule being a structure having a shape factor greater than or equal to 2.5 and formed of an aluminous grain or of several adjacent aluminous grains, an aluminous grain being a grain formed, for more than 40% of its weight, of $Al_2O_3$ and of said additive.

The inventors have in particular discovered that an excellent compromise between the toughness, the hardness and the rupture stress was possible by combining low contents of cerium oxide and of alumina.

A sintered product according to the invention may in particular be manufactured according to a process according to the invention described below.

A sintered product according to the invention may also have one or more of the following optional characteristics:
  the molar content of $Y_2O_3$ is preferably less than 1.9%, preferably less than 1.7%, preferably less than 1.5%, and/or preferably greater than 0.6%, preferably greater than 0.8%, preferably greater than 1%, as a molar percentage on the basis of the sum of $ZrO_2$, $CeO_2$ and $Y_2O_3$;
  the content of alumina $Al_2O_3$ is preferably less than 16%, and/or preferably greater than 11%, preferably greater than 12%, preferably greater than 13%, as a molar percentage on the basis of the oxides;
  the molar content of $CeO_2$ is preferably less than 5%, preferably less than 4.5%, preferably less than 4.2%, preferably less than 4%, preferably less than 3.8%, and/or greater than 3%, as a molar percentage on the basis of the sum of $ZrO_2$, $CeO_2$ and $Y_2O_3$;
  the additive is preferably chosen from CaO, manganese oxides, SrO, BaO and mixtures thereof, preferably from CaO, manganese oxides, and mixtures thereof;
  preferably, the additive is a mixture of CaO on the one hand and of one or more manganese oxides on the other hand;
  the content of additive is preferably greater than 0.3%, preferably greater than 0.4%, preferably greater than 0.5%, and/or preferably less than 5%, preferably less than 4%, as a percentage by weight on the basis of the oxides;
  in one embodiment, the additive comprises CaO, the content of CaO being less than 4%, preferably less than 3%, preferably less than 2%, preferably less than 1%, or else less than 0.8%, or else less than 0.6%, as a percentage by weight on the basis of the oxides;
  in one embodiment, the additive comprises $Nd_2O_3$, the content of $Nd_2O_3$ being less than 4%, preferably less than 3%, preferably less than 2%, preferably less than 1%, or else less than 0.8%, or else less than 0.6%, as a percentage by weight on the basis of the oxides;
  in one preferred embodiment, the additive is a mixture of one or more manganese oxides and of CaO, the content of manganese oxide(s) expressed in the form MnO being greater than 0.2%, preferably greater than 0.3%, and/or preferably less than 4%, preferably less than 3%, preferably less than 2%, preferably less than 1%, preferably less than 0.8%, and the content of CaO preferably being greater than 0.2%, and/or less than 4%, preferably less than 3%, preferably less than 2%, preferably less than 1%, preferably less than 0.8%, preferably less than 0.5%, as a percentage by weight on the basis of the oxides;
  the content of impurities is preferably less than 1.0%, preferably less than 0.8%, preferably less than 0.5%, or else less than 0.3%, as a percentage by weight on the basis of the oxides. In one embodiment the impurities are formed of oxides;

in one embodiment, the content of alumina is greater than 10%, preferably greater than 11%, preferably greater than 12%, preferably greater than 13%, and less than 19%, preferably less than 16%, and the content of $ZrO_2$ partially stabilized with $CeO_2$ and $Y_2O_3$ represents the balance to 100%, $CeO_2$ and $Y_2O_3$ being present in amounts such that, as a molar percentage on the basis of the sum of $ZrO_2$, $CeO_2$ and $Y_2O_3$, the molar content of $Y_2O_3$ is less than 2%, preferably less than 1.9%, preferably less than 1.7%, preferably less than 1.5% and greater than 0.6%, preferably greater than 0.8%, preferably greater than 1%, and the molar content of $CeO_2$ is less than 5.5%, preferably less than 5%, preferably less than 4.5%, preferably less than 4.2%, preferably less than 4%, preferably less than 3.8% and greater than 3%, and the content of additive is greater than 0.2%, preferably greater than 0.3%, preferably greater than 0.4%, or else greater than 0.5% or greater than 0.6%, and less than 5%, preferably less than 4%, preferably less than 3%, preferably less than 2.5%, preferably less than 2%, or else less than 1.5%, or else less than 1%, as a percentage by weight on the basis of the oxides, and the content of impurities is less than 1.0%, preferably less than 0.8%, preferably less than 0.5%, or else less than 0.3%, as a percentage by weight on the basis of the oxides;

in one preferred embodiment, the content of alumina is greater than 10%, preferably greater than 11%, preferably greater than 12%, preferably greater than 13%, and less than 19%, preferably less than 16%, and the content of $ZrO_2$ partially stabilized with $CeO_2$ and $Y_2O_3$ represents the balance to 100%, $CeO_2$ and $Y_2O_3$ being present in amounts such that, as a molar percentage on the basis of the sum of $ZrO_2$, $CeO_2$ and $Y_2O_3$, the molar content of $Y_2O_3$ is less than 2%, preferably less than 1.9%, preferably less than 1.7%, preferably less than 1.5%, and greater than 0.6%, preferably greater than 0.8%, preferably greater than 1%, and the molar content of $CeO_2$ is less than 5.5%, preferably less than 5%, preferably less than 4.5%, preferably less than 4.2%, preferably less than 4%, preferably less than 3.8% and greater than 3%, and the additive is a mixture of a manganese oxide and of CaO, the content of manganese oxide expressed in the form MnO being greater than 0.2%, preferably greater than 0.3% and less than 4%, preferably less than 3%, preferably less than 2%, preferably less than 1%, preferably less than 0.8%, and the content of CaO being greater than 0.2% and less than 4%, preferably less than 3%, preferably less than 2%, preferably less than 1%, preferably less than 0.8%, preferably less than 0.5%, as a percentage by weight on the basis of the oxides, and the content of impurities is less than 1.0%, preferably less than 0.8%, preferably less than 0.5%, or else less than 0.3%, as a percentage by weight on the basis of the oxides;

the mean size of the compact grains is less than 1.5 μm, preferably less than 1 μm, preferably less than 0.5 μm and/or preferably greater than 0.1 μm, preferably greater than 0.2 μm;

in one preferred embodiment, more than 95%, preferably more than 97%, preferably more than 99% by number of the compact grains are grains of partially stabilized zirconia and/or grains formed, for more than 40% of their weight, of alumina;

the mean length of the aluminous elongated nodules is less than 18 μm, preferably less than 15 μm, or else less than 10 μm and/or greater than 1 μm, preferably greater than 2 μm, preferably greater than 5 μm;

more than 50%, preferably more than 60%, preferably more than 70%, preferably more than 80% by number of the aluminous elongated nodules have a shape factor of greater than or equal to 3, or else greater than or equal to 4;

the sintered product has a ratio H, equal to the ratio of the surface covered by the aluminous elongated nodules to the surface covered by said aluminous elongated nodules and the compact grains comprising more than 40% by weight of alumina, expressed as percentages, of greater than 5%, preferably greater than 10%, preferably greater than 20%, and/or preferably less than 95%, preferably less than 90%, preferably less than 80%;

more than 30%, more than 40%, more than 60%, more than 80%, more than 90% by number of the aluminous elongated nodules have a general rectilinear shape;

said aluminous elongated nodules comprise the element Al and the metal cations of the oxides added as additive (Ca and/or Mn and/or Zn and/or Pr and/or Sr and/or Cu and/or Nd and/or Ba and/or Fe);

the bulk density of the sintered product is preferably greater than 5.4 $g/cm^3$, or else greater than 5.5 $g/cm^3$, or else greater than 5.6 $g/cm^3$ and/or preferably less than 6.2 $g/cm^3$, or else less than 6.1 $g/cm^3$, or else less than 6 $g/cm^3$, or else less than 5.8 $g/cm^3$;

the relative density of the sintered product is preferably greater than 95%, preferably greater than 97%, preferably greater than 98%, preferably greater than 99%.

The invention also relates to a process for manufacturing a sintered product according to the invention, comprising the following steps:

a) preparing a feedstock comprising a particulate mixture having a median size of less than 1.0 μm, and the composition of which is adapted so as to obtain, at the end of step c), a sintered product according to the invention, b) shaping the feedstock so as to obtain a preform, c) sintering the preform at a sintering temperature above 1300° C. so as to obtain a sintered product according to the invention.

A process according to the invention may also comprise one or more of the following optional characteristics:

in step a), a step of milling is carried out, preferably by co-milling, so as to obtain a median size of preferably less than 0.8 μm, preferably less than 0.6 μm, preferably less than 0.5 μm, or else less than 0.3 μm, or else less than 0.2 μm;

the process preferably comprises, in step b), a shaping by tape casting or by pressing, preferably by uniaxial pressing, by hot pressing or by isostatic pressing;

in step c), the sintering temperature is preferably below 1600° C., preferably below 1550° C., preferably below 1500° C. and/or above 1350° C., preferably above 1400° C.

The invention also relates to a particulate mixture comprising $ZrO_2$ particles, $Al_2O_3$ particles, $CeO_2$ particles, $Y_2O_3$ particles and CaO particles and/or particles of one or more manganese oxides and/or ZnO particles and/or particles of one or more praseodymium oxides and/or SrO particles and/or particles of one or more copper oxides and/or $Nd_2O_3$ particles and/or BaO particles and/or particles of one or more iron oxides and/or particles of precursors of these oxides, and/or particles of several of these oxides and/or precursors of these oxides, the particulate mixture having a chemical composition suitable for the manufacture of a sintered product according to the invention.

Advantageously, such a particulate mixture is ready to use.

A particulate mixture according to the invention may in particular be packaged in bags.

Preferably, the manganese oxide is chosen from MnO, $MnO_2$, $Mn_2O_3$, $Mn_3O_4$ and mixtures thereof. Preferably, the manganese oxide is chosen from MnO, $Mn_3O_4$ and mixtures thereof.

Preferably, the praseodymium oxide is $Pr_6O_{11}$.

Preferably, the copper oxide is CuO.

Preferably, the iron oxide is chosen from FeO, $Fe_2O_3$ and mixtures thereof.

Preferably, said particulate mixture comprises $ZrO_2$, $Al_2O_3$, $CeO_2$ and $Y_2O_3$ particles, CaO particles and particles of a manganese oxide, preferably of MnO and/or of $Mn_3O_4$, and/or particles of precursors of these oxides, and/or particles of several of these oxides and/or precursors of these oxides.

Preferably, the median size of said particulate mixture is less than 1 µm, preferably less than 0.8 µm, preferably less than 0.6 µm, preferably less than 0.5 µm, or else less than 0.3 µm, or else less than 0.2 µm.

Preferably, the specific surface area of said particulate mixture is less than 20 m$^2$/g, preferably less than 15 m$^2$/g, and/or preferably greater than 5 m$^2$/g.

The invention finally relates to a device chosen from:
a mechanical wearing part, preferably chosen from the group formed by a closure member and a closure member seat of a valve, a pump rotor, a pump seal and a pump body,
a dental article, in particular a tooth prosthesis or a part of an orthodontic appliance,
an optical fiber connector, in particular a ferrule or a sleeve,
a decorative article chosen from the group formed by a jewel, a watch, a bracelet, a necklace, a ring, a brooch, a tie pin, a handbag, a telephone, a piece of furniture, a household utensil, a handle, a button, a veneer, a visible part of a consumer goods item, a part of a spectacle frame, a piece of crockery and a frame,
said device comprising a sintered product according to the invention or manufactured from a particulate mixture according to the invention.

Definitions

The term "particle" is understood to mean an individualized solid product in a powder.

"Sintering" refers to the consolidation, by heat treatment at over 1100° C., of a granular agglomerate, optionally with partial or total melting of some of its constituents (but not of all of its constituents).

The "median size" of a powder, generally denoted by $D_{50}$, refers to the size that divides the particles of this powder into first and second populations of equal weight, these first and second populations only comprising particles having a size greater than or equal to, or less than respectively, the median size. The median size may for example be measured using a laser particle size analyzer.

The "mean size" of the grains of a sintered product refers to the dimension measured according to the "Mean Linear Intercept" method. A measurement method of this type is described in the standard ASTM E1382.

The manganese oxides comprise in particular MnO, $Mn_2O_3$, $MnO_2$ and $Mn_3O_4$.

The iron oxides comprise in particular FeO, $Fe_2O_3$, $Fe_3O_4$.

The praseodymium oxides comprise in particular $Pr_2O_3$.

The copper oxides comprise in particular CuO and $Cu_2O$.

The term "impurities" is understood to mean the inevitable constituents necessarily introduced with the raw materials. In particular, the compounds that belong to the group of oxides, nitrides, oxynitrides, carbides, oxycarbides, carbonitrides and metallic species of sodium and other alkali metals, vanadium and chromium are impurities. As examples, mention may be made of $Na_2O$ or MgO. On other hand, hafnium oxide is not considered to be an impurity.

$HfO_2$ is not chemically separable from $ZrO_2$. In the chemical composition of a product comprising zirconia, $ZrO_2$ therefore denotes the total content of these two oxides. However, according to the present invention, $HfO_2$ is not deliberately added to the feedstock. $HfO_2$ therefore denotes only traces of hafnium oxide, this oxide always being naturally present in sources of zirconia at contents generally of less than 2%. For the sake of clarity, the content of zirconia and of traces of hafnium oxide can be denoted either by $ZrO_2+HfO_2$ or by $ZrO_2$, or else by "zirconia content".

The term "precursor" of an oxide is understood to mean a constituent capable of providing said oxide during the manufacture of a sintered product according to the invention. For example, barium carbonate $BaCO_3$ is a possible precursor of BaO.

The "shape factor of a grain or of a nodule" refers to the ratio between the largest dimension of the grain or of the nodule, or "length", and the largest dimension measured perpendicularly to the direction of said largest dimension, or "width". These dimensions are measured in a viewing plane of a polished section of the sintered product, conventionally on electron microscopy images of this section.

An "elongated nodule" refers to a nodule having a shape factor F greater than or equal to 2.5.

The term "absolute density" of a sintered product according to the invention is understood to mean the absolute density conventionally calculated using a rule of mixtures, from a chemical analysis of said sintered product according to the invention, by considering that all the yttrium and cerium oxides stabilize the zirconia, and without taking into account the additives and the impurities. The absolute density of the zirconia partially stabilized with $Y_2O_3$ and $CeO_2$ is calculated according to the teaching of the document "Phase transformation and lattice constants of zirconia solid solutions in the system $Y_2O_3$—$CeO_2$—$ZrO_2$", Urabe et al., Materials Science Forum Vols. 34-36 (1988) pp 147-152.

The term "relative density" of a product is understood to mean the ratio equal to the bulk density divided by the absolute density, expressed as a percentage.

Unless otherwise mentioned, all the percentages relating to the composition of a product or relating to a feedstock are percentages by weight on the basis of the oxides and all the percentages of $CeO_2$ and $Y_2O_3$ are molar percentages on the basis of the sum of $ZrO_2$, $CeO_2$ and $Y_2O_3$.

Unless otherwise mentioned, all the means are arithmetic means.

The ratio of the mean surface area of the aluminous elongated nodules to the mean surface area of the compact grains, and the ratio of the number of compact grains to the number of aluminous elongated nodules are measured in a viewing plane of a polished section of the sintered product, conventionally on electron microscopy images of this section.

BRIEF DESCRIPTION OF THE FIGURES

Other features and advantages of the invention will become more apparent on reading the following detailed description and on examining the appended drawing in which.

DETAILED DESCRIPTION

Figure 1:
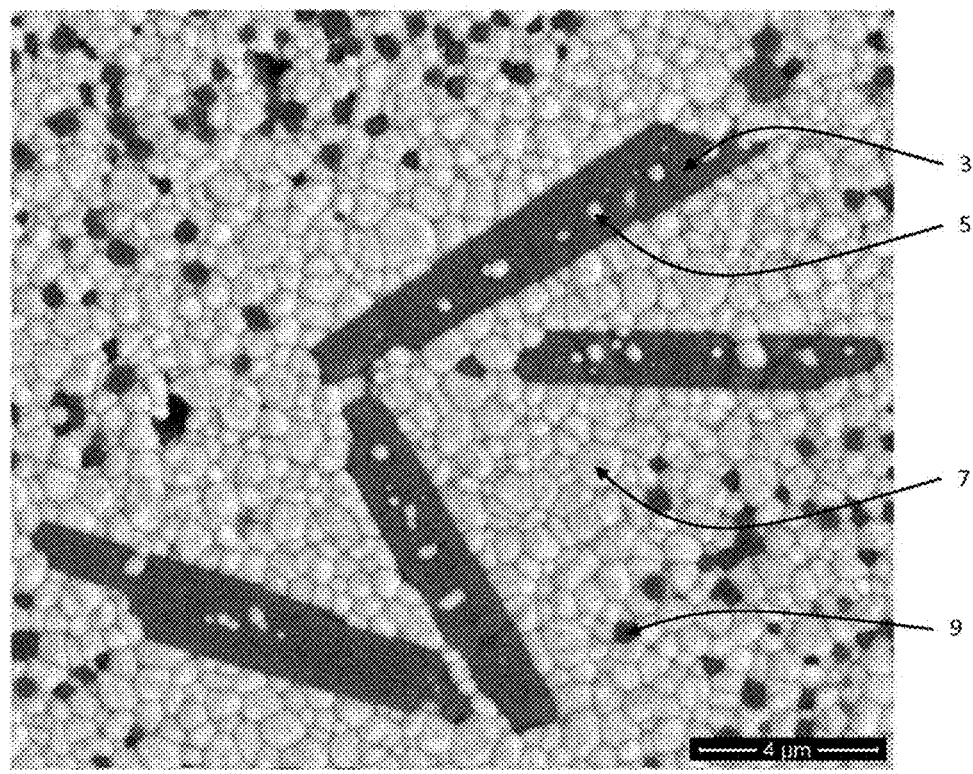
FIGS. 1 and 2 represent photographs of a polished section of the sintered product of example 12, according to the invention, obtained after sintering at a temperature of 1450° C., the sintered product having undergone, after polishing, a thermal treatment at 1400° C. for 30 minutes in order to reveal the grain boundaries.

In order to manufacture a sintered product according to the invention, the steps a) to c) described above, and presented in detail below, may be followed.

In step a), a milling of the raw materials may be necessary in order to obtain a median size, after mixing, of less than 1.0 µm.

In particular, the powders of raw materials providing the oxides may be milled individually or, preferably, co-milled, if they do not meet the desired particle size distribution, and in particular if they have a median size of greater than 1 µm, greater than 0.6 µm, greater than 0.5 µm, greater than 0.3 µm or greater than 0.2 µm. The milling may be carried out in a wet environment, for example in an attrition mill. After wet milling, the milled particulate mixture is preferably dried.

Preferably, in step a), the powders used, in particular the powders of $ZrO_2$, of alumina $Al_2O_3$, of $Y_2O_3$, of $CeO_2$, and of additive each have a median size of less than 5 µm, less than 3 µm, less than 1 µm, less than 0.7 µm, preferably less than 0.6 µm, preferably less than 0.5 µm. Advantageously, when each of these powders has a median size of less than 1 µm, preferably less than 0.8 µm, preferably less than 0.6 µm, preferably less than 0.5 µm, or else less than 0.3 µm, or else less than 0.2 µm, the milling is optional.

The use of powders having a small median size also advantageously enables the sintering temperature to be reduced.

These powders may also be replaced, at least partially, by powders of precursors of these oxides, introduced in equivalent amounts.

Preferably, the zirconia powder used has a specific surface area, calculated by the BET method, of greater than 5 m²/g, preferably greater than 6 m²/g, preferably greater than 7 m²/g, and less than 20 m²/g, preferably less than 15 m²/g. Advantageously, the sintering temperature in step d) is reduced, and the milling, generally in suspension, and suspending operation are facilitated thereby.

The addition of CaO, and/or of a manganese oxide, and/or of ZnO, and/or of a praseodymium oxide, and/or of SrO, and/or of a copper oxide, and/or of $Nd_2O_3$, and/or of BaO, and/or of an iron oxide and/or of precursors of these oxides advantageously makes it possible to increase the amount of aluminous elongated nodules contained in the sintered product and to improve the mechanical performance.

The powders providing the oxides or the precursors are preferably chosen so that the total content of impurities is less than 2%, as a percentage by weight on the basis of the oxides.

In one embodiment, $Y_2O_3$ is introduced at least partly in the form of a zirconia partially stabilized with yttrium oxide.

In one embodiment, $CeO_2$ is introduced at least partly in the form of a zirconia partially stabilized with cerium oxide, or else stabilized with cerium oxide.

As is well known to a person skilled in the art, the feedstock may comprise, in addition to the particulate mixture, a solvent and/or an organic shaping additive and/or a dispersant, the natures and the amounts of which are suitable for the shaping method of step b).

Preferably the solvent is water.

The organic shaping additive may be chosen from polyethylene glycols (or PEGs), polyvinyl alcohols (or PVAs), lattices, cellulose derivatives and mixtures thereof.

The dispersant may for example be a polyacrylate.

All these elements disappear during the subsequent manufacturing steps, possibly leaving however some traces thereof remaining.

In step b), the feedstock is shaped by any technique known to person skilled in the art, preferably by tape casting or by pressing, preferably by uniaxial pressing, by hot pressing or by isostatic pressing. In the case where the feedstock is shaped by pressing, a prior step of drying, for example by spray drying, may be carried out. The size of the spray-dried particles may for example be between 20 µm and 250 µm.

Optionally, the shaping comprises a drying of the preform.

In step c), the preform is sintered at a temperature above 1300° C., preferably above 1350° C., preferably above 1400° C., so as to obtain a sintered product according to the invention. Preferably, the sintering temperature is below 1600° C., preferably below 1550° C., preferably below 1500° C. The sintering is preferably carried out in air at atmospheric pressure.

Preferably, the sintering time is greater than 1 hour, greater than 2 hours, and/or less than 10 hours, less than 7 hours, or less than 5 hours. Preferably, the sintering time is between 2 and 5 hours.

The sintering temperature is preferably proportionally higher when the amount of alumina is substantial.

The inventors have noted the presence of a particular microstructure in the sintered products according to the invention.

As represented in FIG. 1, the microstructure is characterized by the presence of aluminous elongated nodules 3, which may be in the form of substantially rectilinear rods. FIG. 1 also shows inclusion grains 5, in particular grains of zirconia, within the aluminous elongated nodules. The mean length of the aluminous elongated nodules is typically greater than 1 µm and/or less than 20 µm. The microstructure specific to the products according to the invention also comprises compact grains. The compact grains typically have a mean size of less than 2 µm and/or greater than 0.1 µm.

Figure 2:
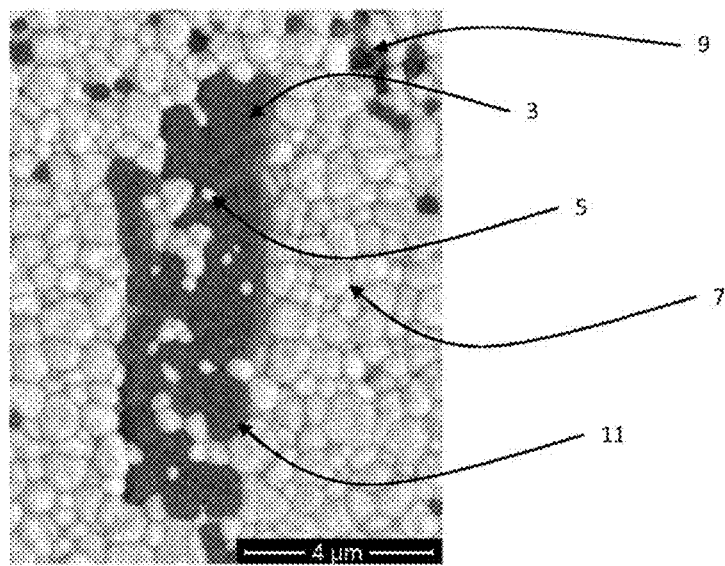

An aluminous elongated nodule 3 may be formed by a grain, as in FIG. 1 or by a cluster of adjacent aluminous grains 11, as in FIG. 2. The aluminous grains 11 have "coalesced" during the sintering. An aluminous grain is preferably formed, for more than 50%, more than 60%, or else more than 70% of its weight, of $Al_2O_3$ and of said additive.

Typically, more than 90%, more than 95%, or else more than 98% or 100% of the weight of the zirconia is in the form of compact grains of zirconia 7. The inventors have noted that more than 60%, preferably more than 80%, more preferably more than 90% of the volume of the zirconia is in the tetragonal phase.

$CeO_2$ and $Y_2O_3$ are used to stabilize the zirconia but may also be present outside thereof.

Preferably, more than 90%, more than 95%, more than 98%, or else substantially 100% of the other compact grains are grains formed, for more than 40% of their weight, of alumina 9.

An analysis has shown that the aluminous elongated nodules 3 comprise aluminum and the metal cations of the oxides added as additive (Ca and/or Mn and/or Zn and/or Pr and/or Sr and/or Cu and/or Nd and/or Ba and/or Fe). Said aluminous elongated nodules may also comprise the element cerium (Ce). Thus, if the additive comprises CaO and a manganese oxide, said aluminous elongated nodules comprise the elements Al, Ca, Mn and Ce.

The inventors have observed that the aluminous elongated nodules are substantially formed, depending on the additive, of a hibonite-type phase and/or of a magnetoplumbite-type phase.

The ratio of the mean surface area of the aluminous elongated nodules to the mean surface area of the compact grains is preferably greater than 5, greater than 10, greater than 20, greater than 30, and/or less than 200, less than 150, less than 100.

The ratio of the number of compact grains to the number of aluminous elongated nodules is preferably greater than 10, greater than 20, greater than 30, greater than 40, greater than 50, and/or less than 2000, less than 1500, less than 1000, less than 500.

Examples

The following nonlimiting examples are given for the purpose of illustrating the invention.

Sintered products were prepared from:
- an yttrium-stabilized zirconia powder containing a molar content of $Y_2O_3$ equal to 3%, having a specific surface area of the order of 10 $m^2/g$ and a median size of less than 0.3 µm for example 1,
- a zirconia powder with a purity of greater than 99%, having a specific surface area of the order of 10 $m^2/g$ and a median size of less than 0.3 µm for example 2,
- an yttrium-stabilized zirconia powder containing a molar content of $Y_2O_3$ equal to 1.2%, having a specific surface area of the order of 8 $m^2/g$ and a median size of less than 5 µm for examples 3 to 16,
- a $CeO_2$ powder with a purity of greater than 99% and having a median size of less than 10 µm for examples 2 to 16,
- an aluminia powder with a purity of greater than 99% and having a median size of less than 0.5 µm for examples 1 to 16,
- a powder of manganese oxides, mainly in the $Mn_3O_4$ form and also containing MnO, with a purity, expressed in the MnO form, of greater than 88%, and more than 90% by weight of the particles of which having a size of less than 44 µm, for examples 3 to 16,
- calcium carbonate powder having a median size equal to 5 µm for examples 3 to 16.

These powders were mixed then co-milled in a wet environment until a particulate mixture having a median particle size of less than 0.3 µm was obtained. Polyvinyl alcohol was then added in an amount equal to 2% on the basis of the solids of the particulate mixture. The feedstock obtained was then spray dried in the form of a powder of spray-dried particles having a median size equal to 60 µm, a relative density of between 30% and 60% and an index of sphericity of greater than 0.85 in a spray dryer, the relative density of a powder of spray-dried particles being the ratio equal to the true density divided by the absolute density, expressed as a percentage; the absolute density of a powder of spray-dried particles being the ratio equal to the weight of solids of said powder after milling to a fineness such that substantially no closed pore remains, divided by the volume of this weight after milling, measured by helium pycnometry, and the true density of a powder of spray-dried particles being the mean of the bulk densities of each spray-dried particle of the powder, the bulk density of a spray-dried particle being the ratio equal to the mass of said spray-dried particle divided by the volume that said spray-dried particle occupies.

In step b), each powder of spray-dried particles was then pressed on a uniaxial press at a pressure equal to 100 MPa.

In step c), the preforms obtained were then transferred to a sintering furnace where they were brought, at a rate of 100° C./h, up to 1450° C. The temperature of 1450° C. was maintained for 2 hours. The drop in temperature was carried out by natural cooling.

Measurement Protocols

The hardness of the sintered products is measured using Vickers indentations at 0.3 kg.

After measuring the length of the radial cracks, the toughness was calculated using the universal formula developed by Liang et al. ("*Evaluation by indentation of fracture toughness of ceramic materials*", 1990).

The 3-point bending modulus of rupture is measured on the sintered products under the conditions of the standard ISO 6872.

The bulk density of the sintered products is measured by hydrostatic weighing.

The chemical analysis of the sintered products is measured by inductively coupled plasma or ICP for elements in an amount that does not exceed 0.5%. In order to determine the content of the other elements, a pearl of the product to be analyzed is manufactured by melting the product, then the chemical analysis is carried out by x-ray fluorescence.

The shape factor of the grains and of the nodules of the sintered products, the mean length of the aluminous elongated nodules and the ratio H equal to the ratio of the surface covered by the aluminous elongated nodules to the surface covered by said aluminous elongated nodules and the grains comprising more than 40% by weight of alumina, are measured on images obtained by backscattered electron scanning electron microscopy, of samples of sintered products, said sections having first been polished until a mirror quality is obtained then thermally treated to reveal the grain boundaries, in a cycle having a rate of temperature increase equal to 100° C./h, to a hold temperature 50° C. below the sintering temperature, maintained for 30 minutes, and a temperature drop by natural cooling. The magnification used for capturing the images is chosen so as to display between 2 and 4 aluminous elongated nodules on one image. 20 images per sintered product were acquired.

The mean size of the grains of the compact sintered products was measured by the mean linear intercept method. A method of this type is described in the standard ASTM E1382. According to this standard, analysis lines are plotted on images of the sintered products, then, along each analysis line, the lengths, referred to as "intercepts", between two consecutive compact grain boundaries cutting said analysis line are measured. The analysis lines are determined so as not to cut the aluminous elongated nodule.

The mean size "d" of the grains of a sintered product is given by the relationship: $d=1.56.l'$. This formula is derived from the formula (13) from "Average Grain Size in Polycrystalline Ceramics", M. I. Mendelson, J. Am. Cerm. Soc. Vol. 52, No. 8, pp. 443-446.

The specific area is measured by the BET (Brunauer Emmet Teller) method as described in Journal of American Chemical Society 60 (1938), pages 309 to 316.

Table 1 below summarizes the results obtained.

TABLE 1

| | Chemical analysis (weight %) | | | | | | | | Mean size of the compact grains ($\mu m$) |
|---|---|---|---|---|---|---|---|---|---|
| | base sum $ZrO_2$ + $CeO_2$ + $Y_2O_3$ (mol %) | | | $ZrO_2$ partially | | Additives | | | |
| Ex | $ZrO_2$ | $CeO_2$ | $Y_2O_3$ | stabilized | $Al_2O_3$ | Manganese oxide expressed in the form MnO | CaO | Impurities | |
| 1 (*) | 97 | 0 | 3 | 79.7 | 20.0 | 0 | 0 | 0.3 | <1 |
| 2 (*) | 88 | 12 | 0 | 97.6 | 2.0 | 0 | 0 | 0.4 | <1 |
| 3 (*) | 94.7 | 4.1 | 1.2 | 73.9 | 24.9 | 0.4 | 0.3 | 0.5 | <1 |
| 4 | 94.9 | 4 | 1.1 | 83.8 | 14.9 | 0.6 | 0.3 | 0.4 | 0.33 |
| 5 (*) | 93.1 | 5.8 | 1.1 | 98.7 | 0.3 | 0.5 | 0.3 | 0.2 | <1 |
| 6 (*) | 93.8 | 5.1 | 1.1 | 95.9 | 3.0 | 0.4 | 0.3 | 0.4 | 0.40 |
| 7 (*) | 97 | 1.8 | 1.2 | 88.8 | 10.1 | 0.5 | 0.2 | 0.4 | <1 |
| 8 (*) | 94.9 | 4 | 1.1 | 94 | 5.0 | 0.5 | 0.3 | 0.2 | <1 |
| 9 (*) | 96.8 | 2 | 1.2 | 83.9 | 14.9 | 0.5 | 0.3 | 0.4 | <1 |
| 10 | 94 | 4.9 | 1.1 | 81.1 | 16.9 | 0.6 | 0.3 | 1.1 | 0.36 |
| 11 | 94 | 4.9 | 1.1 | 88.4 | 10.1 | 0.5 | 0.3 | 0.7 | 0.35 |
| 12 | 93 | 5.9 | 1.1 | 88.1 | 10.5 | 0.4 | 0.3 | 0.7 | 0.44 |
| 13 (*) | 91.4 | 7.5 | 1.1 | 88.7 | 10.2 | 0.4 | 0.4 | 0.3 | <1 |
| 14 (*) | 89.9 | 9 | 1.1 | 89.2 | 10.0 | 0.4 | 0.3 | 0.1 | <1 |
| 15 | 95.5 | 3.4 | 1.1 | 84.7 | 14.1 | 0.5 | 0.3 | 0.4 | <1 |
| 16 (*) | 93.4 | 5.5 | 1.1 | 94 | 5.0 | 0.5 | 0.3 | 0.2 | <1 |

| Ex | Mean length of the aluminous elongated nodules ($\mu m$) | Ratio H (%) | Bulk density (g/cm$^3$) | Relative density (%) | Vickers hardness | Toughness (MPa·m$^{1/2}$) | 3-point bending modulus of rupture (MPa) |
|---|---|---|---|---|---|---|---|
| 1 (*) | — | 0 | 5.39 | 98.1 | 1430 | 8.5 | 780 |
| 2 (*) | — | 0 | 6.08 | 97.1 | 780 | 11 | 560 |
| 3 (*) | 6.0 | 16 | 5.35 | 99.80 | 1390 | 8.7 | |
| 4 | 7.6 | 37 | 5.63 | 99.87 | 1290 | 13.9 | 860 |
| 5 (*) | 7.7 | >95 | 6.11 | 99.78 | 1180 | 13.9 | |
| 6 (*) | 9.1 | >95 | 6.02 | 99.94 | 1180 | 14.4 | |
| 7 (*) | 7.4 | 25 | 5.7 | 98.90 | 1170 | 15.1 | |
| 8 (*) | 6.8 | 84 | 5.92 | 99.59 | 1160 | 16.2 | |
| 9 (*) | 6.2 | 33 | 5.463 | 97.23 | 1130 | 8.2 | |
| 10 | 6.4 | 27 | 5.58 | 99.81 | 1340 | 12.8 | 740 |
| 11 | 6.1 | 58 | 5.78 | 99.72 | 1220 | 12.9 | 780 |
| 12 | 6.5 | 58 | 5.76 | 99.47 | 1260 | 12.7 | 720 |
| 13 (*) | 5.2 | 59 | 5.75 | 98.83 | 1180 | 11.1 | |
| 14 (*) | 6.5 | 62 | 5.79 | 99.16 | 1170 | 8.3 | |
| 15 | 5.7 | 37 | 5.6 | 99.07 | 1280 | 14.1 | 860 |
| 16 (*) | 6.8 | 92 | 5.94 | 99.64 | 1200 | 12.4 | 820 |

(*): examples outside of the invention

Next the mean length "l'" of the intercepts "l" is determined.

For the test below, the intercepts were measured on images, obtained by scanning electron microscopy, of samples of sintered products, said sections having first been polished until a mirror quality is obtained then thermally treated, at a temperature 50° C. below the sintering temperature, to reveal the grain boundaries. The magnification used for capturing the images is chosen so as to display around 100 compact grains on one image. 5 images per sintered product were acquired.

The inventors consider that there is a good compromise between the hardness, the toughness and the 3-point bending modulus of rupture when:
the Vickers hardness is greater than or equal to 1210, and
the toughness is greater than or equal to 10 MPa·m$^{1/2}$, and
the 3-point bending modulus of rupture is greater than or equal to 700 MPa.

Preferably, the hardness is greater than or equal to 1250, and/or the toughness is greater than or equal to 11 MPa·m$^{1/2}$, preferably greater than or equal to 12 MPa·m$^{1/2}$, preferably greater than or equal to 13 MPa·m$^{1/2}$, preferably greater than or equal to 14 MPa·m$^{1/2}$, and the 3-point bending modulus of rupture is greater than or equal to 750 MPa, preferably greater than 800 MPa.

Examples 1 and 2, outside of the invention, show that a sintered product comprising a zirconia partially stabilized with 3 mol % of $Y_2O_3$ and an alumina content equal to 20%, and that a sintered product comprising a zirconia stabilized with 12 mol % of $CeO_2$ and an alumina content equal to 2% respectively do not satisfy the desired compromise.

A comparison of example 3, outside of the invention, and example 4 shows the need for an alumina content of less than 19%. This comparison also makes it possible to observe that for low cerium oxide contents, increasing the amount of alumina beyond 19% leads to an abrupt reduction in the toughness.

Examples 5 and 16 however show the need for a minimum alumina content of greater than 10%.

Examples 7 and 9, outside of the invention, show that a molar content of $CeO_2$ equal to 1.8% and 2% respectively is too low and does not make it possible to achieve the desired compromise.

Examples 13 and 14, outside of the invention, show that a molar content of $CeO_2$ equal to 7.5% and 9% respectively is too high and does not make it possible to achieve the desired compromise. Examples 13 and 14 also show that, for low alumina contents according to the invention, the presence of an amount of cerium oxide of greater than 6.5 mol % leads to an unsatisfactory hardness.

Of all the examples, example 15 is preferred. Example 15 shows that it is particularly advantageous to limit the content of cerium oxide to less than 5%, to less than 4%, and even to less than 3.5%.

As is now clearly apparent, the inventors have discovered that the simultaneous presence of a low content of alumina and a low content of cerium oxide advantageously makes it possible to obtain a sintered product based on alumina and on zirconia that has a good compromise between hardness, toughness and modulus of rupture.

Of course, the invention is not limited to the examples and embodiments described above.

The invention claimed is:

1. A sintered product having a chemical analysis such that, as percentages by weight on a basis of oxides present in the sintered product,
   $ZrO_2$ partially stabilized with $CeO_2$ and $Y_2O_3$: balance to 100%,
   $Al_2O_3$: >10% and <19%
   additive selected from the group consisting of CaO, manganese oxides, ZnO, praseodymium oxides, SrO, copper oxides, $Nd_2O_3$, BaO, iron oxides, and mixtures thereof: 0.2-6%,
   impurities: <2%,
   $CeO_2$ and $Y_2O_3$ being present in amounts such that, as a molar percentage on a basis of a sum of $ZrO_2$, $CeO_2$ and $Y_2O_3$,
   $CeO_2$: ≥2.5 mol % and <5.5 mol %
   $Y_2O_3$: 0.5-2 mol %.

2. The sintered product as claimed in claim 1, wherein a molar content of $CeO_2$ is less than 5% and greater than 3%.

3. The sintered product as claimed in claim 2, wherein a molar content of $CeO_2$ is less than 4%.

4. The sintered product as claimed in claim 1, wherein a molar content of $Y_2O_3$ is less than 1.7% and greater than 1%.

5. The sintered product as claimed in claim 1, wherein a content of alumina $Al_2O_3$ is greater than 11% and less than 16%, as a percentage by weight on the basis of the oxides.

6. The sintered product as claimed in claim 1, wherein a content of the additive is greater than 0.5% and less than 4%, as a percentage by weight on the basis of the oxides.

7. The sintered product as claimed in claim 1, wherein the additive is a mixture of CaO and of one or more manganese oxides.

8. The sintered product as claimed in claim 7, wherein a content of CaO is greater than 0.2% and less than 1%, and wherein the content of manganese oxide(s) expressed in the form MnO is greater than 0.2% and less than 1%.

9. The sintered product as claimed in claim 1, having a microstructure comprising grains, having a particle size distribution such that a mean size of the grains having a shape factor of less than 2.5 is less than 2 µm, and having aluminous elongated nodules, a mean length of the aluminous elongated nodules being less than 20 µm, an aluminous elongated nodule being a structure having a shape factor greater than or equal to 2.5 and formed of an aluminous grain or of several adjacent aluminous grains, an aluminous grain being a grain formed, for more than 40% of its weight, of $Al_2O_3$ and of the additive, the "shape factor of a grain or of a nodule" referring to a ratio between a largest dimension of the grain or of the nodule and a largest dimension measured perpendicularly to a direction of said largest dimension of the grain or of the nodule, said dimensions being measured in a viewing plane of a polished section of the sintered product.

10. The sintered product as claimed in claim 9, said product having aluminous elongated nodules covering a surface, and wherein a ratio of the surface covered by the aluminous elongated nodules to the surface covered by the aluminous elongated nodules and by the grains having a shape factor of less than 2.5 and comprising more than 40% by weight of alumina, expressed as percentages, is greater than 5% and less than 95%.

11. The sintered product as claimed in claim 9, wherein a mean length of the aluminous elongated nodules is greater than 1 µm.

12. The sintered product as claimed in claim 1, manufactured with a process comprising the following steps:
    a) preparing a feedstock comprising a particulate mixture having a median size of less than 1.0 µm,
    b) shaping the feedstock so as to obtain a preform, and
    c) sintering the preform at a sintering temperature above 1300° C. so as to obtain said sintered product,
    said particulate mixture comprising $ZrO_2$ particles, $Al_2O_3$ particles, $CeO_2$ particles, $Y_2O_3$ particles and particles of an additive chosen from CaO, and/or particles of one or more manganese oxides and/or SrO particles and/or BaO particles and/or particles of precursors of these oxides, and/or particles of several of these oxides and/or precursors of these oxides.

13. The sintered product as claimed in claim 12, said particulate mixture comprising $ZrO_2$ particles, $Al_2O_3$ particles, $CeO_2$ particles, $Y_2O_3$ particles, CaO particles and particles of one or more manganese oxides, and/or particles of precursors of these oxides, and/or particles of several of these oxides and/or precursors of these oxides.

14. The sintered product as claimed in claim 12, said particulate mixture having a median size of which is less than 1 µm.

15. A device selected from the group consisting of:
    a mechanical wearing part,
    a dental article,
    an optical fiber connector, and
    a decorative article selected from the group consisting of a jewel, a watch, a bracelet, a necklace, a ring, a brooch, a tie pin, a handbag, a telephone, a piece of furniture, a household utensil, a handle, a button, a veneer, a visible part of a consumer goods item, a part of a spectacle frame, a piece of crockery and a frame, comprising a sintered product as claimed in claim 1.

16. A device selected from the group consisting of:

a mechanical wearing part, a dental article, an optical fiber connector, and a decorative article selected from the group consisting of a jewel, a watch, a bracelet, a necklace, a ring, a brooch, a tie pin, a handbag, a telephone, a piece of furniture, a household utensil, a handle, a button, a veneer, a visible part of a consumer goods item, a part of a spectacle frame, a piece of crockery and a frame, comprising a sintered product manufactured from a particulate mixture comprising $ZrO_2$ particles, $Al_2O_3$ particles, $CeO_2$ particles, $Y_2O_3$ particles and particles of an additive chosen from CaO, and/or particles of one or more manganese oxides and/or SrO particles and/or BaO particles and/or particles of precursors of these oxides, and/or particles of several of these oxides and/or precursors of these oxides, the particulate mixture having a chemical composition suitable for the manufacture of the of a sintered product according to claim 1.

17. The sintered product as claimed in claim 13, wherein the particles of one or more manganese oxides are selected from the group consisting of MnO particles, $Mn_3O_4$ particles, and mixtures thereof.

* * * * *